United States Patent
Lin et al.

(10) Patent No.: US 6,723,189 B2
(45) Date of Patent: *Apr. 20, 2004

(54) PROCESS FOR MAKING A WORK PIECE HAVING A MAJOR PHASE OF α" FROM A TITANIUM ALLOY

(75) Inventors: Jiin-Huey Chern Lin, 911 Tower Rd., Winnetka, IL (US) 60093; Chien-Ping Ju, 16 Pinewood Dr., Carbondale, IL (US) 62901; Chih-Min Lee, Kaohsiung (TW); Wen-Fu Ho, Tainan Hsien (TW); Dan Jae Lin, Taipei (TW); Wen-Wei Cheng, Miaoli (TW); Chia Wei Lin, Tainan (TW); Che Chin Yang, Taipei (TW)

(73) Assignees: Jiin-Huey Chern Lin, Winnetka, IL (US); Chien-Ping Ju, Carbondale, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/157,121

(22) Filed: May 30, 2002

(65) Prior Publication Data

US 2002/0179208 A1 Dec. 5, 2002

Related U.S. Application Data

(63) Continuation-in-part of application No. 10/134,524, filed on Apr. 30, 2002, which is a continuation-in-part of application No. 09/226,204, filed on Jan. 7, 1999, now Pat. No. 6,409,852.

(51) Int. Cl.$^7$ .................................................. C22F 1/18
(52) U.S. Cl. ...................................... 148/669; 148/421
(58) Field of Search ................................. 148/669, 421; 420/421, 417

(56) References Cited

U.S. PATENT DOCUMENTS

| | | | | |
|---|---|---|---|---|
| 4,857,269 A | * | 8/1989 | Wang et al. | 420/417 |
| 4,952,236 A | * | 8/1990 | Wang et al. | 148/2 |
| 5,205,984 A | * | 4/1993 | Rowe | 420/420 |
| 5,415,704 A | * | 5/1995 | Davidson | 148/316 |
| 5,906,692 A | * | 5/1999 | Bhowal et al. | 148/671 |
| 5,954,724 A | * | 9/1999 | Davidson | 606/76 |

* cited by examiner

Primary Examiner—Andrew L. Oltmans
(74) Attorney, Agent, or Firm—Bacon & Thomas, PLLC

(57) ABSTRACT

Quenching a work piece made of a titanium alloy having a temperature higher than 800° C. to a temperature lower than 500° C. at a cooling rate greater than 10° C./second between 800° C. and 500° C. is used to render the cooled work piece containing α" phase as a major phase. The work piece is preferably a medical implant.

11 Claims, 4 Drawing Sheets

PROCESS FOR MAKING A WORK PIECE HAVING A MAJOR PHASE OF α" FROM A TITANIUM ALLOY

CROSS-REFERENCE TO RELATED APPLICATION

The present application is a continuation-in-part application of U.S. patent application Ser. No. 10/134,524, filed Apr. 30, 2002, which is a continuation-in-part application of U.S. application Ser. No. 09/226,204, filed Jan. 7, 1999 now U.S. Pat. No. 6,409,852. The above-listed applications are commonly assigned with the present invention and the entire contents of which are incorporated herein by reference.

FIELD OF THE INVENTION

The present invention is related to a process for making a work piece having a major phase of α" from a titanium alloy, and in particular a process for making a biocompatible low modulus high strength titanium-based medical implant having a major phase of α".

BACKGROUND OF THE INVENTION

Titanium and titanium alloys have been popularly used in many medical applications due to their light weight, excellent mechanical performance and corrosion resistance. The relatively low strength commercially pure titanium (c.p. Ti) is currently used as dental implant, crown and bridge, as well as denture framework. With a much higher strength than c.p. Ti, Ti-6Al-4V alloy has been widely used in a variety of stress-bearing orthopedic applications, such as hip prosthesis and artificial knee joint. Moreover, the lower elastic modulus allows the titanium alloy to more closely approximate the stiffness of bone for use in orthopedic devices compared to alternative stainless steel and cobalt-chrome alloys in orthopedic implants. Thus, devices formed from the titanium alloy produce less bone stress shielding and consequently interfere less with bone viability.

Various attempts at providing low modulus, high strength titanium alloys for making medical implants with less stress shielding have been proffered by the prior art. There is still a great interest in finding a lower modulus and higher strength titanium alloys. In addition, studies have reported that the release of Al and V ions from the medical implants might cause some long-term health problems, for example the low wear resistance of Ti-6Al-4V alloy could accelerate the release of such harmful ions. Therefore, a primary objective of the present invention is to provide a process for making a work piece, and in particular a biocompatible low modulus high strength medical implant, from a titanium alloy free from potential harmful components.

SUMMARY OF THE INVENTION

The present invention provides a process for making a work piece having a major phase of α" from a titanium alloy comprising the following steps:
quenching a work piece having a temperature higher than 800° C. to a temperature lower than 500° C. at a cooling rate greater than 10° C./second between 800–500° C., so that the cooled work piece contains α" phase as a major phase, wherein said work piece is made of a titanium alloy selected from the group consisting from the following a), and b):
a) a titanium-molybdenum (Ti—Mo) alloy consisting essentially of 6–9 wt % of Mo, and the balance titanium;
b) a titanium-niobium (Ti—Nb) alloy consisting essentially of 10–30 wt % of Nb, and the balance titanium.

Preferably, said cooling rate is greater than 20° C.
Preferably, said quenching comprises water quenching.
Preferably, said work piece has a temperature of 800–1200° C. before said quenching.
Preferably, the process of the present invention further comprises casting said titanium alloy to form said work piece having a temperature higher than 800° C. prior to said quenching.
Preferably, 6. the process of the present invention further comprises metal working said titanium alloy, and heating the resulting work piece to form said work piece having a temperature higher than 800° C. prior to said quenching.
Preferably, said titanium alloy further comprises one or more incidental impurities selected from the group consisting of carbon, oxygen and nitrogen, wherein a total amount of said one or more incidental impurities is less than 1 wt %.
Preferably, said work piece having a major phase of α" is a medical implant.
Preferably, said titanium alloy is a).
Preferably, said titanium alloy is b), and more preferably said titanium alloy contains 13–28 wt % of niobium.

BRIEF DESCRIPTION OF THE DRAWINGS

The invention will be described in conjunction with the following drawings wherein.

DETAILED DESCRIPTION OF THE PREFERRED EMBODIMENTS

The present invention provides a process for making a biocompatible low modulus high strength medical implant from a titanium alloy, which comprises preparing a titanium alloy having a composition consisting essentially of 7–9 wt % of Mo, and the balance titanium, or consisting essentially of 10–30 wt % of Nb, and the balance titanium; casting or metal working the titanium alloy to form a work piece; and quenching the resulting hot cast having a temperature higher than 800° C. or heating the work piece resulted from said metal working to a temperature higher than 800° C. at a cooling rate greater than 10° C. per second, so that the cooled work piece contains α" phase as a major phase, and can be used as a medical implant which is biocompatible, and has a low modulus and high strength.

The casting and the metal working suitable for use in the process of the present invention are not limited, and can by any known techniques in the art.

A typical quenching method used in the process of the present application is water quenching; however, any methods known in the art which have a cooling rate greater than 10° C., preferably 20° C., per second, can also be used.

The medical implant prepared by the process of the present invention can be an orthopedic implant, a dental implant, a dental crown, a dental bridge or a denture framework.

Two of the preferred embodiments according to the present invention will be described in the following examples, that are intended as illustrative only since numerous modifications and variations therein will be apparent to those skilled in the art.

EXAMPLE 1

Ti-7.5Mo alloy (7.5 wt % Mo) was prepared from a commercially pure titanium (c.p. Ti) bar, and molybdenum of 99.95% using a commercial arc-melting vacuum-pressure type casting system (Castmatic, Iwatani Corp., Japan). The melting chamber was first evacuated and purged with argon. An argon pressure of 1.5 kgf/cm$^2$ was maintained during melting. Appropriate amounts of the c.p. Ti bar and molybdenum wire (92.5 wt % Ti-7.5 wt % Mo) were melted in a U-shaped copper hearth with a tungsten electrode. The ingot was re-melted three times to improve chemical homogeneity.

Figure 1:
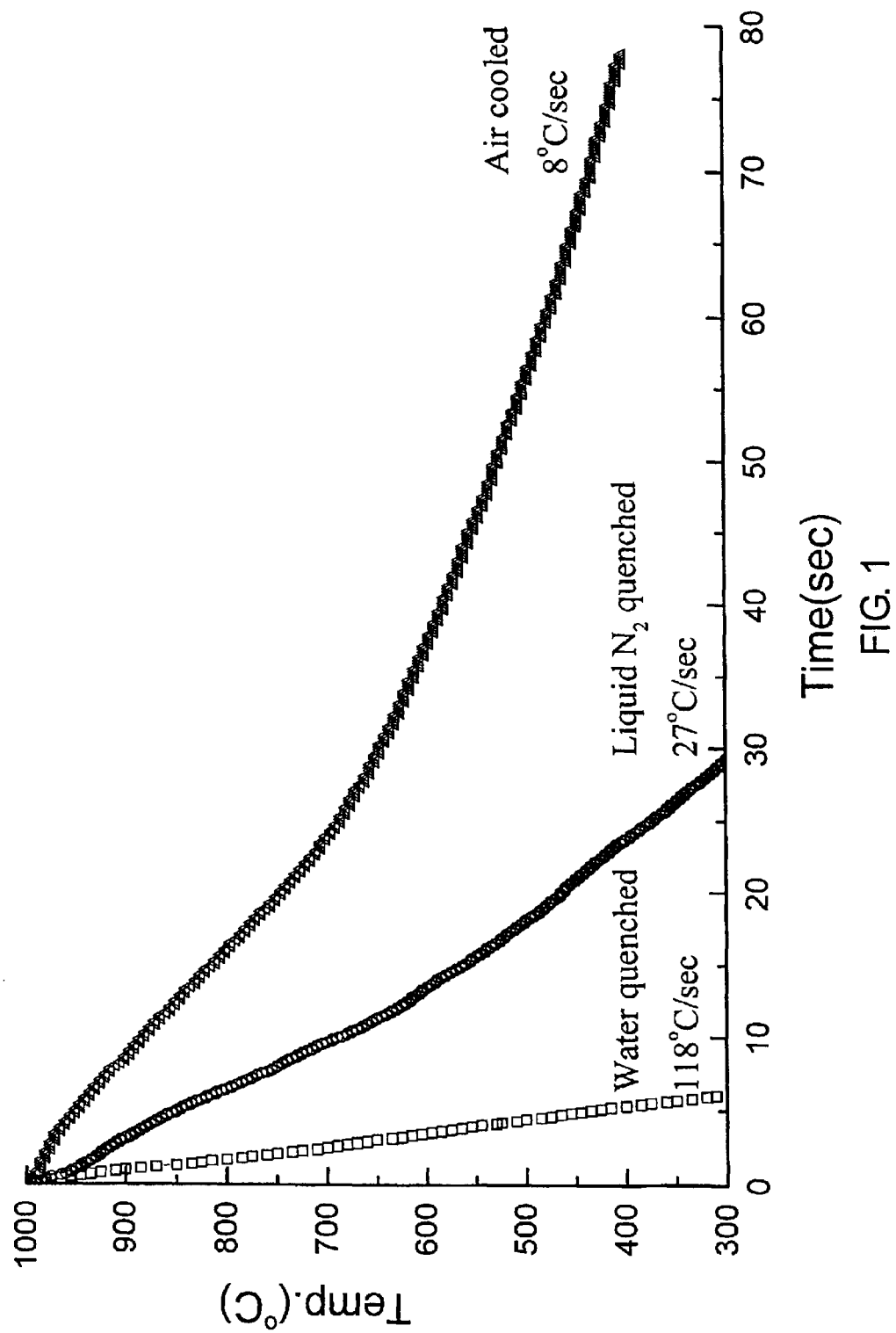
FIG. 1 is a plot showing the average cooling rates between 900–500° C. of a Ti-7.5Mo alloy (7.5 wt % Mo) via water quenching, liquid nitrogen quenching and air cooling.

A specimen having an outer diameter of 7 mm and a length of 29 mm was prepared from the Ti-7.5Mo alloy, at one end of which was further provided with a hole having a diameter of 3.5 mm and a depth of 12 mm for mounting a K-type thermal couple therein. A titanium in the form of a sponge was received in a quartz tube and fixed at a bottom thereof by a quartz cap, and the specimen equipped with the thermal couple was inserted into the quartz tube and hermetically mounted inside the quartz tube with one end of the thermal couple being connected to a temperature recorder (ss. 250 Recorder, Sekonic, Japan). The quartz tube at the sealed end was further equipped with a vacuum pump, and a vacuum meter. The quartz tube was vacuumed for five minutes, and placed in an air furnace (s19, Nabertherm®, Germany) preheated at 1000° C. for 30 minutes. The quartz tube was removed from the air furnace, and the specimen together with the thermal couple was subjected to water quenching, liquid nitrogen quenching or air cooling. The average cooling rates recorded are shown in FIG. 1.

Figure 2:
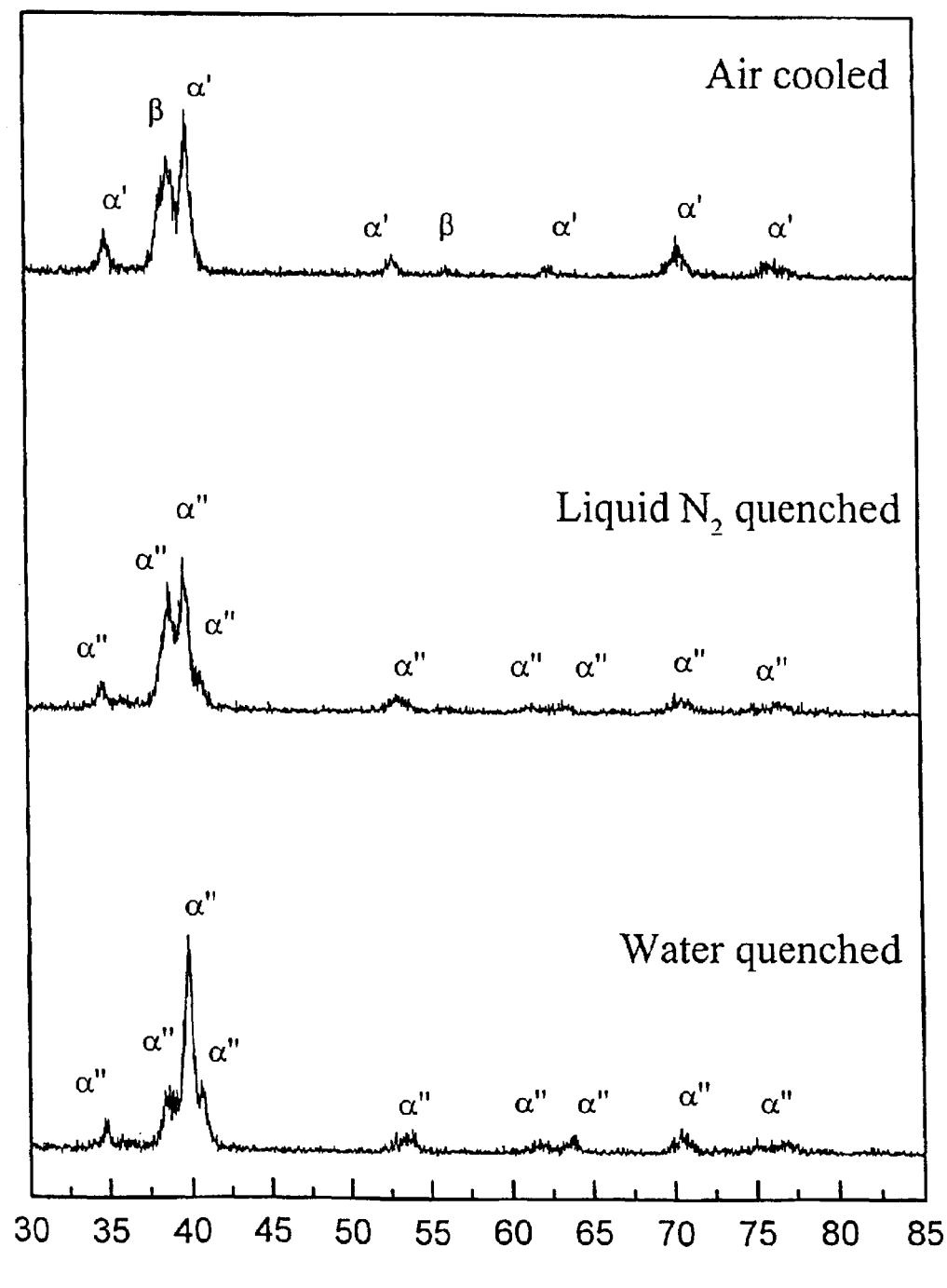
FIG. 2 shows X-ray diffraction spectra of the specimens of Ti-7.5Mo alloy subjected separately to water quenching, liquid nitrogen quenching and air cooling, at a scanning speed of 3°/min.

X-ray diffraction (XRD) for phase analysis of the cooled specimen was conducted using a Rigaku diffractometer (Rigaku D-max IIIV, Rigaku Co., Tokyo, Japan) operated at 30 kV and 20 mA. A Ni-filtered CuK$_\alpha$ radiation was used for this study. A silicon standard was used for calibration of diffraction angles. Scanning speed of 3°/min was used. The phases were identified by matching each characteristic peak in the diffraction pattern with the JCPDS files. The results are shown in FIG. 2, and are summarized in Table 1.

EXAMPLE 2

Ti-20Nb alloy containing 20 wt % of Nb and the balance Ti was prepared from a commercially pure titanium (c.p. Ti) bar, and niobium wire using a commercial arc-melting vacuum-pressure type casting system (Castmatic, Iwatani Corp., Japan). The melting chamber was first evacuated and purged with argon. An argon pressure of 1.5 kgf/cm$^2$ was maintained during melting. Appropriate amounts of the c.p. Ti bar and niobium wire (80 wt % Ti-20 wt % Nb) were melted in a U-shaped copper hearth with a tungsten electrode. The ingot was re-melted three times to improve chemical homogeneity.

Figure 3:
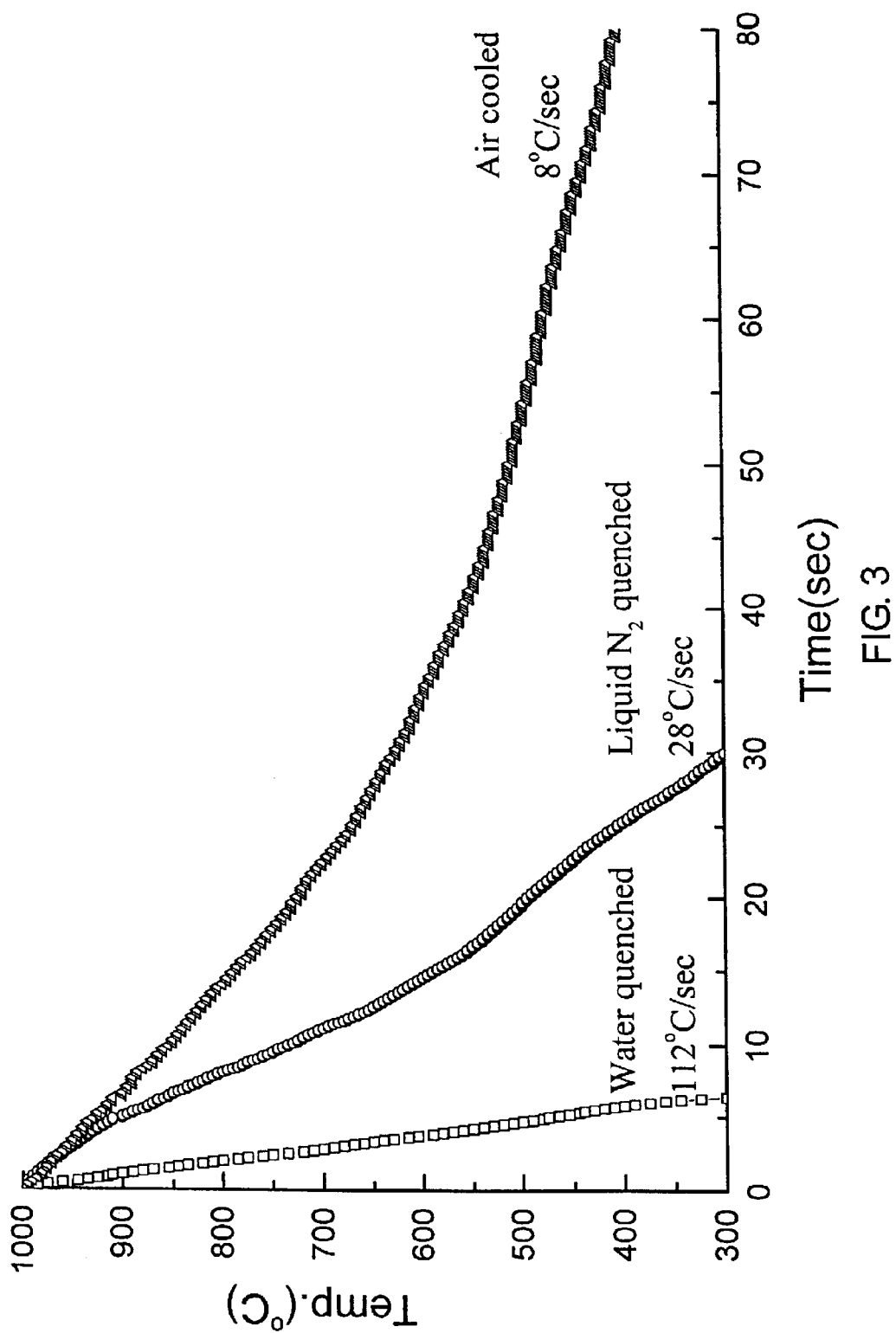
FIG. 3 is a plot showing the average cooling rates between 900–500° C. of a Ti-20Nb alloy (20 wt % Nb) via water quenching, liquid nitrogen quenching and air cooling.
Figure 4:
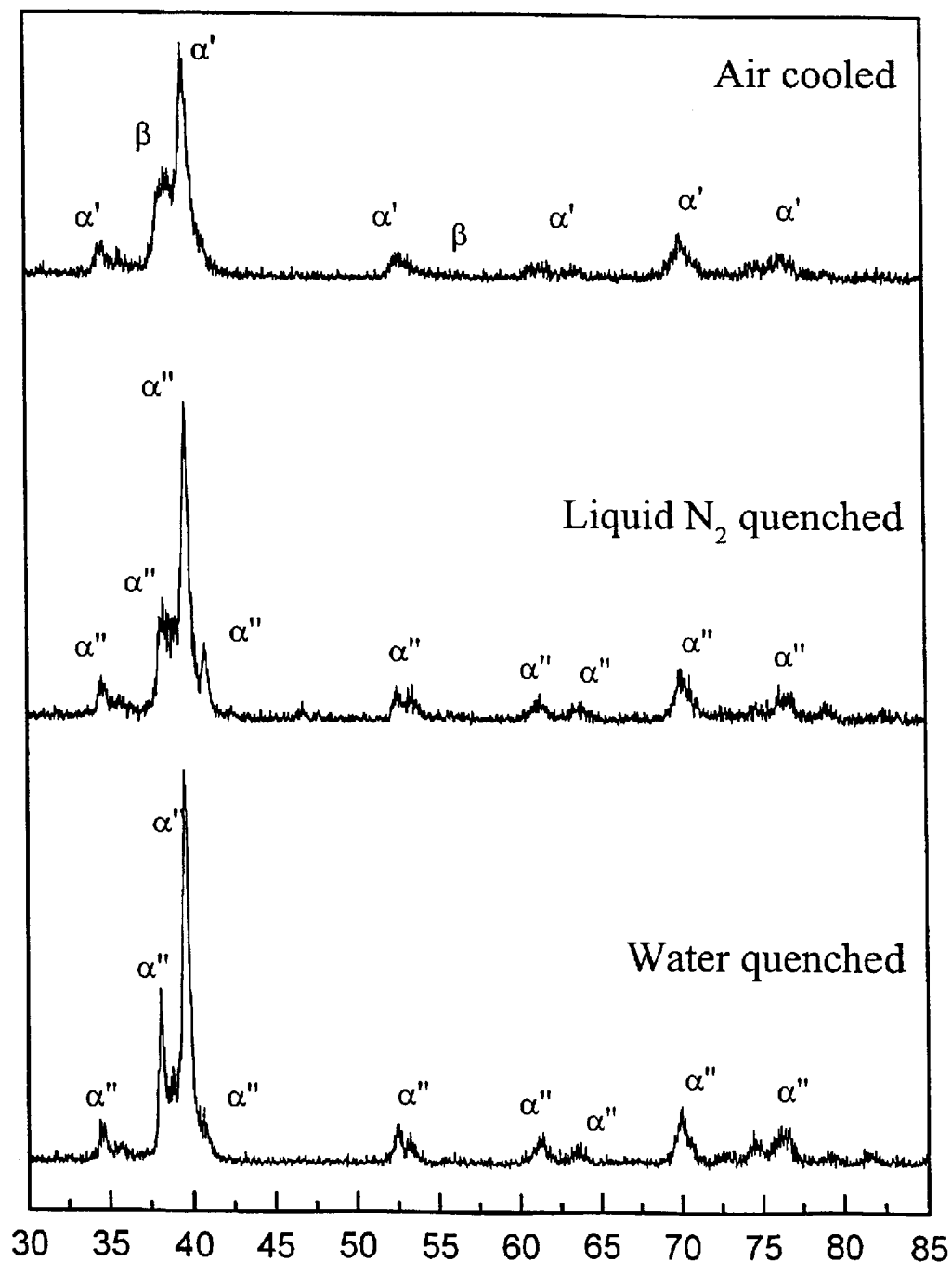
FIG. 4 shows X-ray diffraction spectra of the specimens of Ti-20Nb alloy subjected separately to water quenching, liquid nitrogen quenching and air cooling, at a scanning speed of 3°/min.

A specimen having a shape similar to the Ti-7.5Mo specimen used in Example 1 was prepared from the Ti-20Nb alloy. The Ti-20Nb specimen was heated, cooled and phase analyzed according to the procedures in Example 1. The results are shown in FIG. 3, FIG. 4, and are summarized in Table 1.

TABLE 1

| Sample code | Average cooling rate, ° C./sec | Phase |
|---|---|---|
| Ti-7.5Mo | 118 | α" |
|  | 27 | α" |
|  | 8 | α' + β |
| Ti-20Nb | 118 | α" |
|  | 28 | α" |
|  | 8 | α' + β |

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

What is claimed is:

1. A process for making a work piece having a major phase of α" from a titanium alloy comprising the following steps:
    quenching a work piece having a temperature higher than 800° C. to a temperature lower than 500° C. at a cooling rate greater than 10°C./second between 800–500° C., so that the cooled work piece contains α" phase as a major phase, wherein said work piece is made of a titanium alloy selected from the group consisting from the following a), and b):
    a) a titanium-molybdenum (Ti—Mo) alloy consisting essentially of 6–9 wt % of Mo, and the balance titanium;
    b) a titanium-niobium (Ti—Nb) alloy consisting essentially of 10–30 wt % of Nb, and the balance titanium.

2. The process according to claim 1, wherein said cooling rate is greater than 20° C.

3. The process according to claim 2, wherein said quenching comprises water quenching.

4. The process according to claim 1, wherein said work piece has a temperature of 800–1200° C. before said quenching.

5. The process according to claim 1 further comprising casting said titanium alloy to form said work piece having a temperature higher than 800° C. prior to said quenching.

6. The process according to claim 1 further comprising metal working said titanium alloy, and heating the resulting work piece to form said work piece having a temperature higher than 800° C. prior to said quenching.

7. The process according to claim 1, wherein said titanium alloy further comprises one or more incidental impurities selected from the group consisting of carbon, oxygen and nitrogen, wherein a total amount of said one or more incidental impurities is less than 1 wt %.

8. The process according to claim 1, wherein said work piece having a major phase of α" is a medical implant.

9. The process according to claim 1, wherein said titanium alloy is a).

10. The process according to claim 1, wherein said titanium alloy is b).

11. The process according to claim 10, wherein said titanium alloy contains 13–28 wt % of niobium.

* * * * *